United States Patent [19]
Spears

[11] Patent Number: 5,381,786
[45] Date of Patent: Jan. 17, 1995

[54] METHOD AND APPARATUS FOR MEASUREMENT OF LUMINAL DIMENSIONS

[75] Inventor: James R. Spears, Bloomfield Hills, Mich.

[73] Assignee: Wayne State University, Detroit, Mich.

[21] Appl. No.: 16,611

[22] Filed: Feb. 11, 1993

[51] Int. Cl.6 .......................... A61B 1/06; G01C 5/00
[52] U.S. Cl. ............................... 128/6; 128/4; 356/1
[58] Field of Search ............... 128/4, 6, 7–10, 128/656, 657, 658, 772; 358/98, 107; 356/1

[56] References Cited

U.S. PATENT DOCUMENTS

| | | | |
|---|---|---|---|
| 4,271,829 | 6/1981 | Heckele | 128/6 |
| 4,588,294 | 5/1986 | Siegmund | 128/6 X |
| 4,676,231 | 6/1987 | Hisazumi et al. | 128/6 |
| 4,782,818 | 11/1988 | Mori | 128/6 |
| 4,943,275 | 7/1990 | Stricker | 604/96 |
| 4,980,763 | 12/1990 | Lia | 128/6 X |
| 5,116,317 | 3/1992 | Carson, Jr. et al. | 604/96 |
| 5,150,254 | 9/1992 | Saitou | 128/6 X |
| 5,202,758 | 4/1993 | Tamburrino | 358/98 |

FOREIGN PATENT DOCUMENTS

| | | | |
|---|---|---|---|
| 1629053 | 2/1991 | U.S.S.R. | 128/6 |
| 1717099 | 3/1992 | U.S.S.R. | 128/6 |

OTHER PUBLICATIONS

J. Spears et al., "Coronary Angioscopy During Cardiac Catheterization", 6 JACC, 93 (Jul. 1985).

J. Spears et al., "In Vivo Coronary Angioscopy", 1 J. Am. Coll. Cardiol., 1311 (1983).

Primary Examiner—Stephen R. Crow
Assistant Examiner—John P. Leubecker
Attorney, Agent, or Firm—Brooks & Kushman

[57] ABSTRACT

A method and apparatus for measuring luminal dimensions through visualization of a lumen during fiberoscopy. The method comprises the steps of positioning a fiberscope having a distal end within the lumen; providing a means of support for a means for delivering electromagnetic energy, the support means extending along the lumen beyond the distal end of the fiberscope; emitting a transverse ring of electromagnetic radiation from the support means at a known distance from the distal end of the fiberscope, the ring of electromagnetic radiation becoming incident upon a discrete cross section of a luminal surface of the lumen; and visualizing a ring of electromagnetic radiation reflected from the luminal surface. The apparatus of the present invention comprises an apparatus for measuring luminal dimensions through visualization of a lumen during fiberoscopy. The apparatus comprises a fiber scope having a distal end within the lumen, a means for delivering electromagnetic energy positioned in cooperation with the means of support, the support means extending along the lumen beyond the distal end of the fiber scope, a transverse ring of electromagnetic radiation emitted from the support means at a known distance from the distal end of the fiber scope, the ring of electromagnetic radiation becoming incident upon a discrete section of a luminal surface of the lumen, and a ring of electromagnetic radiation reflected from a luminal surface.

14 Claims, 3 Drawing Sheets

- BROKEN OPTICAL FIBERS
- GUIDING CATHETER
- ATHEROMATOUS PLAQUE

METHOD AND APPARATUS FOR MEASUREMENT OF LUMINAL DIMENSIONS

TECHNICAL FIELD

This invention relates to method and apparatus for measuring luminal dimensions. More specifically, the invention relates to a method for measuring luminal dimensions through visualization of a lumen during fiberoscopy.

BACKGROUND ART

During angioscopy, there are two problems which limit the potential utility of the procedure: 1) Although the vessel cross-section if visualized directly, unlike the case with angiography, the size of the cross-section can be assessed currently only subjectively, because (a) the size of the cross-section varies markedly with the lens-object distance, and (b) different portions of the circumference of a cross-section are often difficult to recognize as belonging to the same cross-section; and 2) The light source during endoscopic procedures is provided at the distal end of the fiberscope, and forward propagation of light down the lumen allows inspection, after displacement of blood by translucent crystalloids, of the luminal surface by light reflected back to the imaging fiberoptic bundle. However, the surface of proximal structures reflects light more strongly than distal ones (inverse square of distance relationship), resulting in excessive reflected light proximal to a lesion of interest.

SUMMARY OF THE INVENTION

This invention relates to a method for measuring luminal dimensions through visualization of a lumen during fiberoscopy, comprising the steps of positioning a fiberscope, having a distal end, within the lumen; providing a means of support for a means for delivering electromagnetic energy, the support means extending beyond the distal end of the fiberscope; emitting a transverse ring of electromagnetic radiation from the support means at a known distance from the distal end of the fiberscope, the ring of electromagnetic radiation becoming incident upon a discrete cross section of an interior surface of the lumen; visualizing a ring of electromagnetic radiation reflected from the luminal surface.

A guidewire used during percutaneous angioplasty procedures has been modified in a novel manner to permit radial emission of light from a specified portion of the wire near its distal end, in order to facilitate diagnostic and therapeutic procedures wherein a ring of light is used to provide quantitative assessment of the luminal cross-sectional area of a discrete vessel segment of interest during angioscopy. A different modification of the emitted light can be used to provide uniform light diffusely along the length of a vessel for improved qualitative angioscopic visualization. Potential therapeutic applications of the cylindrically diffuse light include laser balloon angioplasty and photodynamic therapy.

BEST MODE FOR CARRYING OUT THE INVENTION

Figure 1:
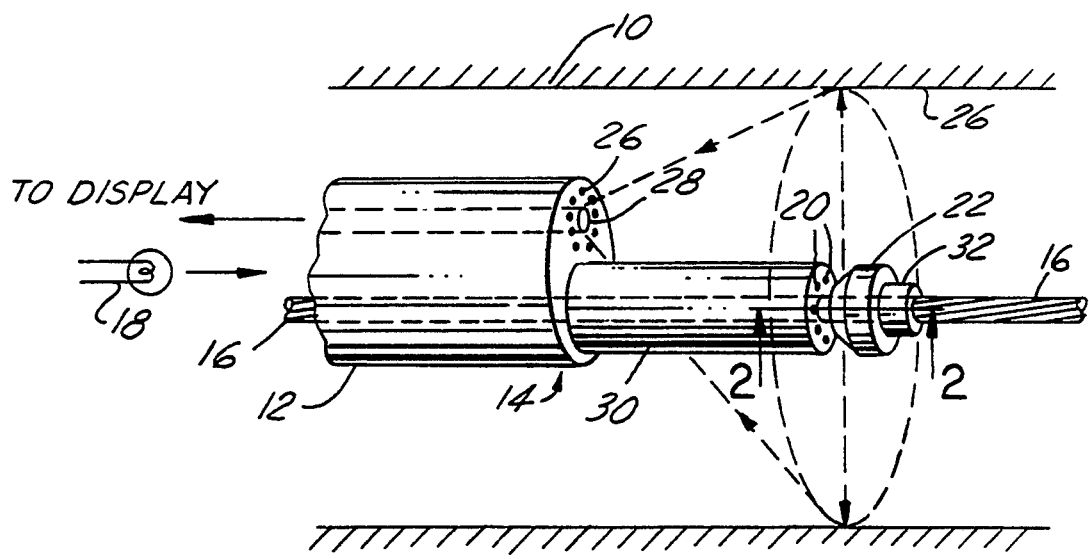
FIG. 1 is a perspective view of an apparatus for measuring luminal dimensions through visualization of an arterial lumen during angioscopy.

Turning first to FIG. 1, there is depicted the environment of the invention disclosed and claimed. That environment includes a lumen 10, the internal diameter of which is to be measured through visualization during fiberoscopy.

A fiberscope 12 is positioned within the lumen 10. As shown, the fiberscope has a distal end 14. A means of support 16, such a guidewire, is provided for a means 20 such as fibers, for delivering electromagnetic energy. The support means 16 extends beyond the distal end 14 of the fiberscope 12.

As illustrated, source 18 provides electromagnetic radiation which is passed axially within the lumen and is emitted from the fibers 20 at a known distance from the distal end 14 of the fiberscope 12. The electromagnetic radiation then impinges upon a frustoconical reflector 22. The electromagnetic radiation then travels transversely until it impinges upon an interior wall of the lumen 10 and is reflected.

The ring of reflected electromagnetic radiation is then visualized as shown by fiberoptic bundle 28. Fibers 26 deliver white light for general examination of lumen 10 and to aid in positioning fiberscope 12.

Upon obtaining a magnification factor derived from a lens-object distance, and measuring a dimension of the reflected ring image, the disclosed method proceeds by deriving the corresponding true luminal dimension utilizing the magnification factor.

The present invention overcomes prior art problems with the use of a "lightwire." Two basic designs are employed, corresponding to solving the two problems encountered during angioscopy.

Figure 5:
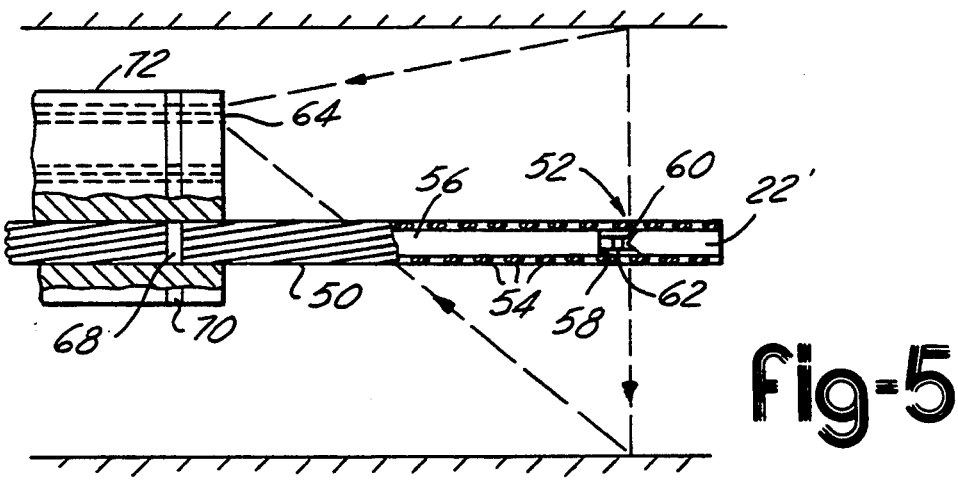
FIG. 5 is a cross-sectional view of an alternate embodiment of the present invention.
Figure 5B:
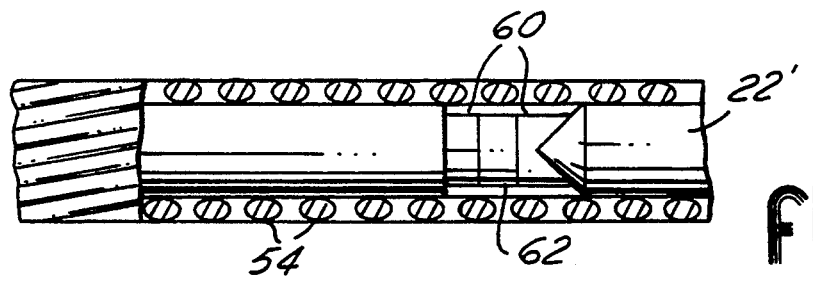
FIG. 5b is an exploded view illustrating a portion of of FIG. 5 in greater detail.

When quantitative evaluation of a discrete luminal cross-section is desired, a ring of light is emitted from the guidewire 50 (FIG. 5) through a small space 52 between adjacent spiral loops of the coils 54 comprising the hollow guidewire, best illustrated in FIG. 5 and 5b. Light is delivered to the space 52 from the fiberoptic 56, the distal end of which can be configured in a wide variety of terminations which result in radial emission of light through the space. For example, light emitted from a flat cleave can be reflected off the inner aspect of the coils 54 and thence into the space 52 between the adjacent spiral loops of the wire.

Alternatively, a diffusing tip 60 which terminates at the distal end of the fiberoptic propagates the light in a radial direction through the space 52 between the loops. Collimation of the light in an axial direction can be achieved by use of an appropriately narrow space 52 between the loops of wire and additionally by covering the diffusing tip proximal and distal to a short window 62 with reflective material (such as gold coating); the window 62 on the diffusing tip and space 52 in the guidewire are aligned to improve the degree of collimation, resulting in a relatively sharp image of a ring of light. As before, reflected light is captured by a fiberoptic bundle via lens 64.

When viewing the lumen with white light, either with a conventional light source or with a diffusing tip 60, the emitted discrete ring of light is visible virtually only by its reflection on the luminal surface of the vessel cross-section corresponding to the axial location of the space 52 between the spiral loops of guidewire 50.

A radio-opaque marker 68 on the guidewire 50 would allow the guidewire 50 to be fluoroscopically positioned accurately relative to the lens of the angioscope by aligning the marker 68 on the wire with a marker 70 on the angioscope 72. Thus, the exact distance between the ring of light reflected on a vessel cross-section of interest and the lens of the angioscope will be known, so that the area bounded by the ring of light can be determined quantitatively utililzing the magnification factor obtained from the graph of FIG. 6. The ring of light typically would be an easily identified color, such as the light from a red or green helium-neon laser source coupled to the proximal end of the fiberoptic. Determination of the cross-sectional area could be performed in an automated fashion by digitizing the video angioscopic image, with the use of algorithms for recognition of the color and measurement of the area encompassed by the ring of light.

Withdrawal or advancement of the angioscope 72 and guidewire together allows determination of the cross-sectional area of multiple contiguous cross-sections, utilizing the same magnification factor so that a plot of cross-sectional area versus axial location could be achieved quickly and accurately.

The lightwire is also used to provide improved white light visualization of the lumen over multiple cross-sections. Fiberoptic 56 with uniform cylindrical diffusing tip 60, typically 1-2 cm in length for a coronary artery application, will have been placed in a distal portion of the interior of a hollow guidewire 50, corresponding to the location along the wire where the coils 54 have been separated by a small space 52 over the same length, thereby permitting radial emission of light through the wire. Unlike a conventional light source, all cross-sections of the vessel along this length are illuminated uniformly, so that interpretation of reflected light is enhanced.

The cylindrically diffused light source provided by the latter modification may be used to perform therapeutic procedures which use light, including either visible, infrared, or ultraviolet radiation. For example, for use as a light source during laser balloon angioplasty, the lightwire would be positioned within the central channel of a balloon catheter corresponding to the body of the balloon. The transparent nature of the materials comprising the central channel, fluid in the balloon, and the balloon would allow transmission of the radiation (typically near infrared from a laser source) through the balloon catheter to the arterial wall. In a different application, the diffusing lightwire may be used to activate a photosensitive drug within the arterial wall, and the lightwire in this instance could be placed either freely within the lumen of the vessel segment of interest or positioned axially in the central channel of a translucent balloon as for laser balloon angioplasty. Typically, red light for activation of a photosensitive drug such as a porphyrin preparation and ultraviolet light for activation of drugs such as psoralens would be provided from a laser source, although techniques for coupling incoherent light to the input end of the fiberoptic could be employed.

Figure 2:
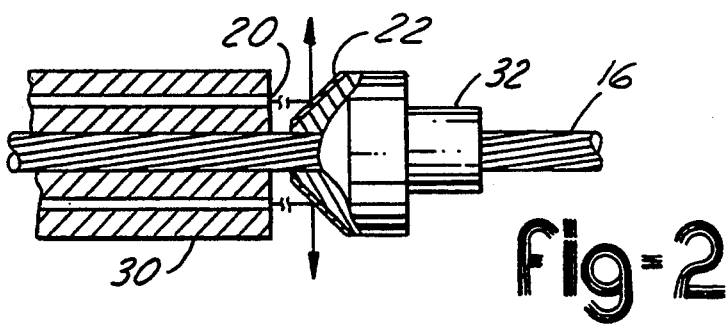
FIG. 2 is a cross-section of the apparatus of FIG. 1 taken along the line 2—2 thereof.
Figure 3:
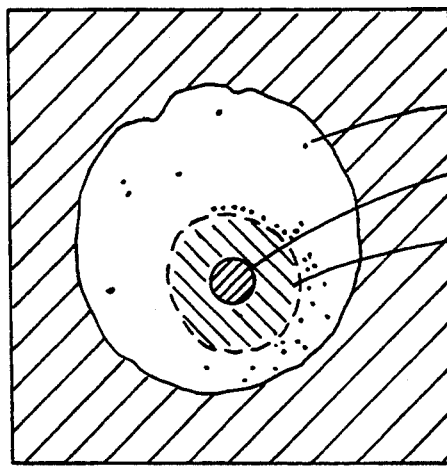
FIG. 3 is a schematic representation of a video frame captured during angioscopic viewing of a coronary artery wherein the angioscope can be passed no further than 5 millimeters from the end of the guiding catheter, depicted therein as a small circle within the angioscopic view. White atheromatous plaque encroaches on the dark residual lumen (black dots are present as a result of broken optical fibers)

In the preferred embodiment of the invention (FIG. 5), the fiberoptic 56 lies within the hollow interior of a guidewire 50, which helps protect the fiberoptic from mechanical damage. However, the fiberoptic 56 could be placed on the external surface of the guidewire (FIGS. 1-2). By terminating the fiberoptic in a cylindrical diffusing tip 60, a radially symmetric light source (either a ring of light or a strong radially diffused light pattern) may be provided despite the fact that the fiberoptic 56 may not be centrally located within the guidewire 50 (FIG. 5). The fiberoptic 56 may be attached to the guidewire 50 with the use of either a flexible epoxy or an external thin plastic sheath. Alternatively, the fiberoptic could be positioned on the external surface of the solid proximal portion of a guidewire and the distal portion of the fiberoptic could be made to enter a distal hollow portion of the guidewire, such as by passing through a small space between adjacent helical loops of the guidewire.

It should be apparent that the two basic patterns of light emitted from the guidewire could be achieved simultaneously with the use of two different fiberoptics incorporated in the same guidewire, so that an axially diffuse white light for viewing multiple luminal cross-sections could be provided along with a discrete ring of light of a specific color during a period of angioscopic observation.

Figure 6:
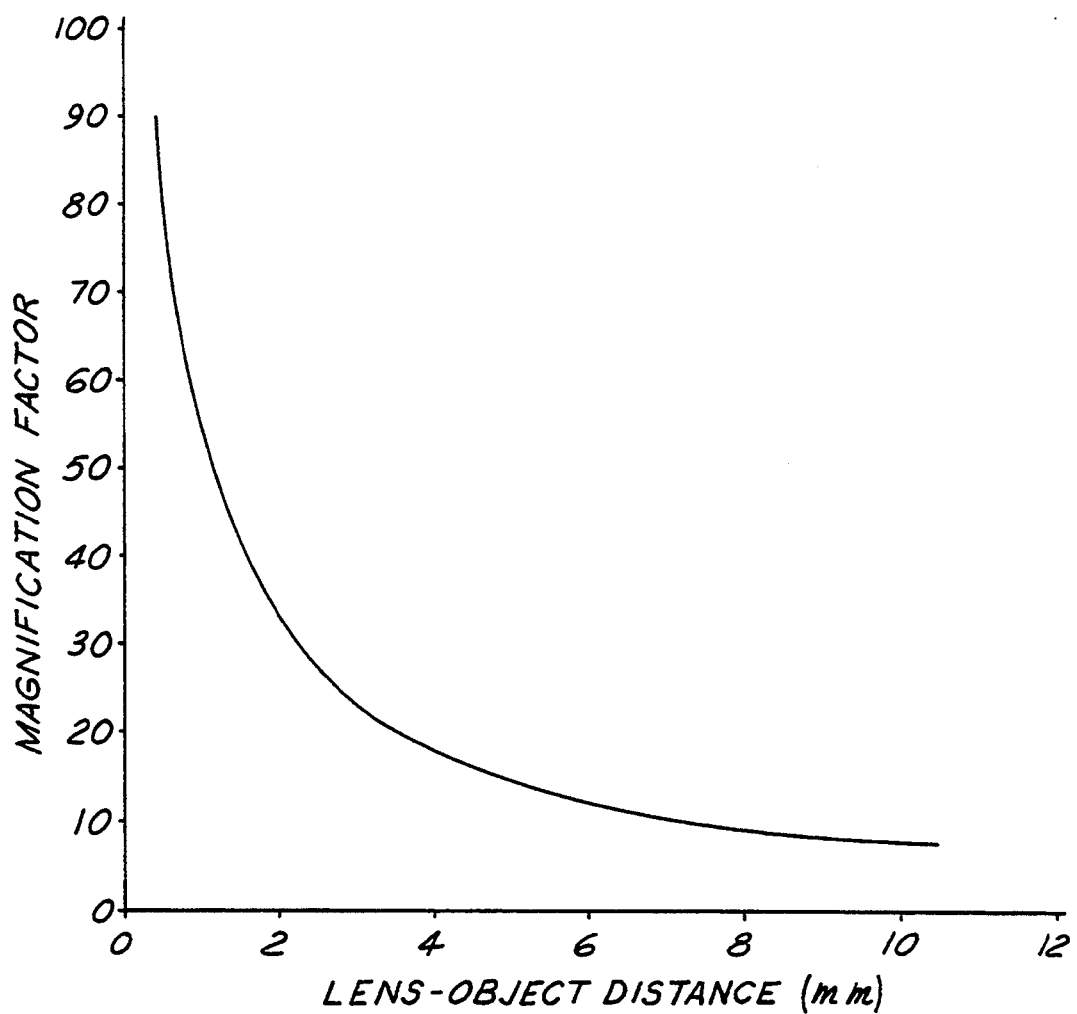
FIG. 6 is a graph of magnification factor versus distance of the object from the distal end of an fiberscope.

An attractive design for delivering a ring of light intraluminally is shown in FIG. 1. A translucent tube 30 is attached to the distal end of the Baxter angioscope 12 so that the lumen in the angioscope for passage of a guidewire 16 is parallel with the lumen of the tube 30. The angioscope contains two flexible plastic tubes between which one or more optical fibers 20 are sandwiched. Preferably, translucent heat shrink tubing is used for the outer tube 30. The fiberoptic(s), with or without an optical coupling medium, such as an appropriate translucent epoxy, propagate light in a forward direction, and the beveled proximal surface 22 of a highly reflective band (also sandwiched between the two plastic layers), such as gold or platinum, directs the light in a perpendicular direction, thereby producing a ring of light normal to the long axis of the tubings. The lumen of the inner plastic tubing 32 allows passage of a variety of angioplasty guidewires. Since the distance of the ring of light from the distal end 14 of the angioscope is fixed, the magnification of the light ring will be accurately known (and provided by the angioscope manufacturer). Thus, the graph of FIG. 6 is not needed for this embodiment. A practical working distance is 3 mm to 10 mm. The length of the tubing, including the enclosed metal band, is therefore only several millimeters longer. The metal band would serve additionally as a radiopaque marker for fluoroscopic identification of the distal tip of the tubing and would facilitate correlation of the axial position of the light ring with the angiographic anatomy.

Figure 4:
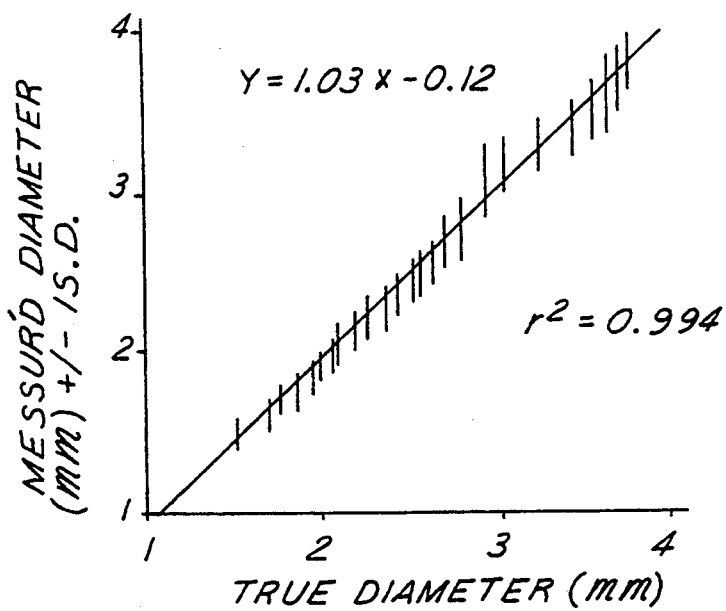
FIG. 4 is a graph of true luminal diameter versus measured diameter. The Figure illustrates that measurement of true luminal diameter for the disclosed method is accurate to within 65±35 microns (±1 S.D.) over a clinically relevant range (1–4 millimeters). The mean coefficient of variation was 6%.

The discrete ring of light produced by the apparatus and method of the present invention provides accurate, repeatable results in measuring intraluminal dimensions. FIG. 4 illustrates that the disclosed apparatus and method is accurate to within 65±35 microns over a clinically relevant range. The data of FIG. 4 were obtained by measuring lumens of known diameters utilizing the method and apparatus of the present invention.

The source of light 18 could be coherent laser light or incoherent light. In the case of the latter, filter(s) could be used to provide a desired color. The ring of light could be used not only to determine luminal dimensions, but also to elicit fluorescence from tissue e.g., with the use of a UV light source. Additional components of a fluorescence detection system might then include an image intensifier; pulsed UV radiation for excitation and fluorescence detection temporarily between pulses with the same fiberoptics which deliver the fluorescence radiation; and related equipment such as an optical multichannel analyzer for on-line detection and analysis of the fluorescence emission spectrum. Both native fluorescence of tissue and drug-induced fluorescence could be examined with the ring of light. Examples of fluorescent drug uptake by arterial tissues include porphyrins, tetracyclines, and Evan's blue dye. The latter could also be examined by its characteristic blue color in regions of the luminal surface where endothelial permeability is abnormal.

Among numerous potential applications of the light ring not mentioned above include: 1) on-line measurement of luminal area/diameter for measurement of vessel wall compliance by plotting arterial pressure against luminal dimensions; and 2) tissue ablation when the intensity of the radiation is greatly increased. In the latter case, fluorescence feedback (either auto-fluorescence of drug-induced fluorescence) could be used to discriminate plaque from plaque-free tissues. Laser radiation could be coupled separately into the fiberoptics, so that selected, discrete portions of the circumference of an arterial cross-section of interest could be ablated independent of the remainder of the cross-section.

What is claimed is:

1. A method for measuring dimensions of a lumen utilizing a fiberscope having a distal end positioned within the lumen during fiberoscopy, the fiberscope also having means for delivering electromagnetic energy so as to irradiate an interior luminal surface, which means extends beyond the distal end of the fiberscope, the method comprising the steps of:
   emitting a radially propagating ring of electromagnetic radiation without substantial axial propagation from the means for delivering electromagnetic energy at a known distance from the distal end of the fiberscope, the ring of electromagnetic radiation impinging upon a discrete interior surface of the lumen so as to form a ring of reflected electromagnetic radiation;
   visualizing the ring of reflected electromagnetic radiation;
   measuring a dimension of the ring of reflected electromagnetic radiation; and
   applying a magnification factor to the measured dimension so as to determine an actual luminal dimension, the magnification factor being derived from said known distance from the distal end of the fiberscope.

2. The method of claim 1 wherein the electromagnetic radiation is in the form of incoherent broadband light.

3. The method of claim 2 wherein the radially propagating ring of broadband light is delivered by a fiberoptic means.

4. The method of claim 1 wherein the electromagnetic radiation is laser radiation.

5. The method of claim 4 wherein the laser radiation is fiberoptically delivered.

6. The method of claim 1 wherein the electromagnetic energy delivered is collimated before the radially propagating ring is emitted to provide a discrete band of electromagnetic energy.

7. The method of claim 1 wherein the step of emitting a radially propagating ring of electromagnetic radiation is performed by a frustoconical reflector mounted upon the supporting means so that the electromagnetic energy is directed into a discrete band thereabout.

8. The method of claim 1 further comprising the step of collimating the electromagnetic radiation in an axial direction before emitting the radially propagating ring of electromagnetic radiation by utilizing a diffusing tip covered with reflective material proximal and distal to a short window.

9. The method of claim 1 further comprising the step of:
   providing a coiled guidewire having a space between adjacent coils wherein the step of emitting a radially propagating ring includes reflecting the electromagnetic energy off an inner aspect of the coils so that the electromagnetic energy passes between adjacent coils.

10. Apparatus for measuring luminal dimensions of an interior wall through visualization of a lumen during fiberoscopy, the apparatus comprising:
    a fiberscope having a distal end adapted to be disposed within the lumen and a means for visualizing beyond the distal end;
    means for delivering electromagnetic energy disposed within the fiberscope and having a distal end extending beyond the distal end of the fiberscope;
    means for supporting said means for delivering electromagnetic energy, the supporting means also disposed within the fiberscope and extending beyond the distal end of said means for delivering; and
    means for forming a radially propagating ring of electromagnetic radiation without substantial axial propagation which impinges upon the interior wall of the lumen at a known distance from the distal end of the fiberscope, said radially propagating ring being reflected so as to form a reflected ring of electromagnetic radiation, the reflected ring being visualized and measured to determine an actual luminal dimension utilizing said known distance.

11. The apparatus of claim 10 wherein said means for visualizing comprises:
    a screen display in communication with the fiberscope for providing an image of the reflecting surface for enabling a measurement to be taken thereof.

12. The apparatus of claim 10 further comprising:
    a collimator mounted upon the supporting means for providing a discrete band of electromagnetic energy.

13. The apparatus of claim 10 wherein the supporting means includes a radio-opaque marker positioned a known distance from the distal end of the means for delivering electromagnetic energy and wherein the fiberscope includes a radio-opaque marker for facilitating alignment of the supporting means relative to the fiberscope.

14. The apparatus of claim 10 wherein the means for delivering electromagnetic energy to the lumen includes:

a diffusing tip which terminates the distal end of the means for delivering electromagnetic energy so as to radially direct electromagnetic energy into a discrete band thereabout.

* * * * *